(12) United States Patent
Lohray et al.

(10) Patent No.: US 7,872,019 B2
(45) Date of Patent: Jan. 18, 2011

(54) POLYMORPHS AND AMORPHOUS FORM OF (S)-(+)-CLOPIDOGREL BISULFATE

(75) Inventors: Braj B. Lohray, Gujarat (IN); Vidya B. Lohray, Gujarat (IN); Bipin Pandey, Gujarat (IN); Mayank G. Dave, Gujarat (IN)

(73) Assignee: Cadila Healthcare Limited, Gujarat (IN)

( * ) Notice: Subject to any disclaimer, the term of this patent is extended or adjusted under 35 U.S.C. 154(b) by 776 days.

(21) Appl. No.: 10/548,712

(22) PCT Filed: Mar. 12, 2003

(86) PCT No.: PCT/IN03/00053

§ 371 (c)(1), (2), (4) Date: Aug. 14, 2006

(87) PCT Pub. No.: WO2004/081016

PCT Pub. Date: Sep. 23, 2004

(65) Prior Publication Data

US 2007/0037842 A1 Feb. 15, 2007

(51) Int. Cl.
*A61K 31/44* (2006.01)
*C07D 515/02* (2006.01)

(52) U.S. Cl. ................................ 514/301; 546/114
(58) Field of Classification Search ............... 546/114; 514/301
See application file for complete search history.

(56) References Cited

U.S. PATENT DOCUMENTS 4,847,265 A 7/1989 Badorc et al.
6,429,210 B1 8/2002 Bousquet et al.
6,635,763 B2 10/2003 Pandey et al.
2002/0177712 A1 11/2002 Pandey et al.
2003/0114479 A1 6/2003 Lifshitz-Liron et al.
2006/0264636 A1 11/2006 Lohray et al.
2007/0037842 A1 2/2007 Lohray et al.
2007/0082924 A1 4/2007 Lohray et al.

FOREIGN PATENT DOCUMENTS

WO 03 051362 A 6/2003

OTHER PUBLICATIONS

Grant, "Theory & origin of polymorphism" in *Polymorphism in Pharmaceutical Solids* (*Drugs & Pharmaceutical Sciences Series*) (Brittain ed.), vol. 95, pp. 8-9 (1999).
Brittain "Methods for characterization of polymorphs and solvates" in *Polymorphism in Pharmaceutical Solids* (*Drugs & Pharmaceutical Sciences Series*) (Brittain ed.), vol. 95, pp. 227-229 (1999).
Byrn et al. "Solid-state pharmaceutical chemistry" *Chem. Mater.*, vol. 6, pp. 1148-1158 (1994).
Byrn et al. *Solid-State Chemistry of Drugs*, Academic Press, pp. 3-9 (1982).
Dunitz & Bernstein "Disappearing polymorphs" *Acc. Chem. Res.*, vol. 28, pp. 193-200 (1995).
Hancock & Zografi "Characteristics and significance of the amorphous state in pharmaceutical systems" *J. Pharm. Sci.*, vol. 86, pp. 1-12 (1997).
Byrn et al. *Solid-State Chemistry of Drugs*, Academic Press, pp. 10-27 (1982).
Knapman "Polymorphic predictions" *Modern Drug Discovery*, vol. 3, pp. 53-54 and 57, four sheets (2000).
Guillory "Generation of polymorphs, hydrates, solvates, and amorphous solids" in *Polymorphism in Pharmaceutical Solids* (*Drugs & Pharmaceutical Sciences Series*) (Brittain ed.), vol. 95, pp. 207-219 (1999).

*Primary Examiner*—Janet L. Andres
*Assistant Examiner*—Raymond Covington
(74) *Attorney, Agent, or Firm*—Nixon & Vanderhye, P.C.

(57) ABSTRACT

The present invention relates to new polymorphs of S-(+)-Clopidogrel bisulfate and a process for preparing the same.

33 Claims, 6 Drawing Sheets

FIGURE – 1    X-Ray Diffractogram of Amorphous (S)-(+)-Clopidogrel Bisulfate

FIGURE-2 IR of Amorphous (S)-(+)-Clopidogrel Bisulfate

FIGURE – 3   X-Ray Diffractogram of chirally pure (ee 99.7 %) Form I of (S)-(+)-Clopidogrel Bisulfate FIGURE – 4  X-Ray Diffractogram of chirally pure (ee 99.7 %) Form II of (S)-(+)-Clopidogrel Bisulfate FIGURE – 5    X-Ray Diffractogram of Form I enriched Amorphous (S)-(+)-Clopidogrel Bisulfate

FIGURE 6

POLYMORPHS AND AMORPHOUS FORM OF (S)-(+)-CLOPIDOGREL BISULFATE

This application is the U.S. national phase of international application PCT/IN2003/000053 filed 12 Mar. 2003 which designated the U.S.

FIELD OF INVENTION

The present invention describes new forms of (S)-(+)-Clopidogrel bisulfate; processes for their preparation and pharmaceutical compositions containing them. More particularly, the present invention reveals new amorphous polymorphs of (S)-(+)-Clopidogrel bisulfate, processes to prepare amorphous forms of (S)-(+)-Clopidogrel bisulfate and various pharmaceutical compositions containing amorphous form of (S)-(+)-Clopidogrel bisulfate. This invention further describes processes for the preparation of other crystalline polymorphs of S-(+)-Clopidogrel bisulfate, Form I, Form II and mixtures of amorphous and Form I and Form II and pharmaceutical compositions containing them. (S)-(+)-Clopidogrel bisulfate an antiplatelet drug is currently being marketed for the treatment of atherosclerosis, mycocardial infarcation, strokes and vascular death. The present invention also describes the method of treatment of such cardiovascular disorders using new polymorphs or mixtures thereof, of (S)-(+)-Clopidogrel bisulfate and pharmaceutical compositions containing them. The present invention relates to the use of new polymorphs of (S)-(+)-Clopidogrel bisulfate disclosed herein and pharmaceutical compositions containing them for the treatment of cardiovascular disorders.

BACKGROUND TO THE INVENTION

The compound of the invention referred herein by its generic name Clopidogrel bisulfate corresponds to the empirical formula $C_{16}H_{16}ClNO_2S \cdot H_2SO_4$ and has a molecular weight 419.9. Chemically it is methyl (+)-(S)-alpha-(2-chlorophenyl)-6,7-dihydrothieno[3,2-c]pyridine-5(4H)-acetate sulfate (1:1), having the following structural formula Clopidogrel is an inhibitor of platelet aggregation and is marketed as an antianginal agent, antiplatelet agent and is found to decrease morbid events in people with established atherosclerotic cardiovascular disease and cerebrovascular diseases.

The therapeutic application of Clopidogrel as blood-platelet aggregation inhibiting agents and antithrombotic agent and its preparation is disclosed in U.S. Pat. No. 4,529,596.

U.S. Pat. No. 4,847,265 describes the process for the preparation of the hydrogen sulfate salt of clopidogrel.

Various other strategies to prepare Clopidogrel are disclosed in WO 98/51681, WO 98/51682, WO 98/51689, WO 99/18110, U.S. Pat. Nos. 5,036,156, 5,132,435, 5,139,170, 5,204,469 and 6,080,875.

We have recently disclosed novel processes for the manufacture of (S)-(+)-Clopidogrel bisulfate (Indian Patent Applications 335/MUM/2001 and 630/MUM/2001).

U.S. Pat. No. 4,847,265 discloses that the dextrorotatory enantiomer of formula (I) of Clopidogrel has an excellent antiagregant platelet activity, whereas the corresponding levorotatory enantiomer of (I) is less tolerated of the two enantiomers and is less active. U.S. Pat. No. 4,847,265 relates to the dextrorotatory enantiomer and its pharmaceutically acceptable salts with platelet aggregation inhibiting activity. However, the precision of determination of laevoenantiomer in dextrorotatory enantiomer was not less than 4%, implying thereby that the method used by the inventors cannot distinguish precisely a sample of S:R ratio 96:4 from a sample having the two enantiomers in the ratio 99.5:0.5 (refer page 5, line 35-50, U.S. Pat. No. 4,847,265). Current regulatory requirements, however, require a high chiral purity (ee not less than 99%) for chiral drugs.

Subsequently filed Patent Application WO 99/65915 (U.S. Pat. No. 6,429,210) titled "Polymorphic Clopidogrel hydrogensulfate form", which is herein incorporated by reference, discloses the existence of a specific polymorphic Form II of the hydrogen sulfate of (S)-(+)-Clopidogrel (m.p.=176±3° C.). It is also disclosed in this patent application that the earlier processes described in the U.S. Pat. No. 4,847,265 gives Form I (m.p. 184±3° C.). These two crystalline polymorphic forms I and II differed in their stability, physical properties, spectral characteristics and their method of preparation, however, both the polymorphs have similar bioavailability, as shown in their bioequivalence in healthy human volunteers.

Although U.S. Pat. No. 4,847,265 reports the formation of (S)-(+)-Clopidogrel bisulfate salt with m.p. 184° C., it was disclosed as Form I only in patent application WO 99/65915. However, a reproducible and consistent method for the preparation of Form I with chirally pure material (ee>99%) was in doubt since chiral purity of the material (Clopidogrel bisulfate) with m.p. 184±3° C., disclosed in U.S. Pat. No. 4,847,265 was not precisely known (degree of imprecision 4% as discussed above.).

In fact, we have observed that formation of Form I of (S)-(+)-Clopidogrel bisulfate with chiral purity>99% ee) is inconsistent and difficult to reproduce using the procedures reported in U.S. Pat. No. 4,847,265 and WO 99/65915 whereas the formation of Form II is extremely facile and consistent with optically pure (S)-(+)-Clopidogrel free base.

Therefore it is very essential to find an alternate polymorphic form which can be consistently produced with high optical purity (ee>99%).

In the present invention, we wish to disclose that formation of form I of Clopidogrel bisulfate is quite reproducible and consistent, if the optical purity is low (S:R=96:4) as reported in U.S. Pat. No. 4,847,265. Therefore, it is imperative to prepare another polymorph of Clopidogrel bisulfate with high optical purity (>99% ee). The present invention describes a new amorphous form of (S)-(+)-Clopidogrel bisulfate having optical purity greater than 99% (ee).

Crystalline solids normally require a significant amount of energy for dissolution due to their highly organized, lattice like structures. For example, the energy required for a drug molecule to escape from a crystal is more than from an amorphous or a non-crystalline form. It is known that the amorphous forms in a number of drugs exhibit different dissolution characteristics and in some cases different bioavailability patterns compared to the crystalline form (Konno T., *Chem. Pharm. Bull.*, 1990; 38: 2003-2007). For some therapeutic indications, one bioavailability pattern may be favoured over another. Therefore, it is desirable to have amorphous forms of drugs and a highly reproducible processes for their preparation.

SUMMARY OF THE INVENTION

Accordingly, the present invention provides new amorphous form of Clopidogrel bisulfate. Another objective of the present invention is to develop a process for the preparation of amorphous polymorphs of (S)-(+)-Clopidogrel bisulfate.

Yet another object is to develop a process for the preparation of a mixture of the new polymorphs described herein with Form I.

Yet another object is to develop a process for the preparation of a mixture of the new polymorphs described herein with Form II.

As an embodiment of the present invention pharmaceutical compositions containing the new forms described in the present invention is provided. There is also provided a composition comprising a Clopidogrel bisulfate crystallization inhibitor composite.

Also is provided a method of treatment and use of the new polymorphs of Clopidogrel for the treatment of cardiovascular disorders, comprising administering, for example, orally a composition of the invention in a therapeutically effective amount.

The main objective of the present invention is to disclose a novel amorphous form of (S)-(+)-Clopidogrel bisulfate.

The amorphous form presented in this invention is non-sticky, free flowing, pharmaceutically processable and stable with distinct physico-chemical properties.

In an embodiment of the present invention processes to manufacture amorphous (S)-(+) Clopidogrel bisulfate, disclosed in the specification is provided.

In another embodiment of the invention process to manufacture a mixture of Form I enriched with amorphous S-(+)-Clopidogrel bisulfate is disclosed.

Another object of the present invention is to disclose processes which may lead to the mixture of amorphous and Form I in the ratio ranging from 0:100 to 100:0.

Still another object of the present invention is to disclose processes, which may lead to the mixture of amorphous and Form II in the ratio ranging from 0:100 to 100:0.

Still another aspect of the present invention, involves the conversion of amorphous (S)-(+)-Clopidogrel bisulfate to Form I.

Yet another object of the invention involves conversion of amorphous (S)-(+) Clopidogrel bisulfate to Form II.

DESCRIPTION OF INVENTION

The present invention provides a novel amorphous form of (S)-(+)-Clopidogrel bisulfate. The term "amorphous", as used herein, relates to solid material which lacks a regular crystalline structure. In a powder X-ray diffractogram such material gives no good intensity peaks. Without being bound by theory, it is believed and also observed that the amorphous solids offer the advantages of faster dissolution due to reduced dissolution energy requirement. Rapid dissolution is important for poorly soluble compounds administered orally, since there is a direct correlation between dissolution rate and bioavailability. Numerous instances have been recorded where only the amorphous form has adequate bioavailability.

Amorphous (S)-(+)-Clopidogrel bisulfate of the present invention can be prepared by any suitable process, not limited to processes described herein.

Amorphous drug substance of the present invention can be precipitated from solution or obtained from melt of compound by carrying out the solidification in such a way, so as to avoid the thermodynamically preferred crystallization process. Such interferences in the process can be brought about by freeze-drying, spray drying and various other processes discussed below.

Amorphous forms can also be prepared by disrupting an existing crystal structure e.g. Form I of (S)-(+)-Clopidogrel bisulfate. This leads to excess free energy and entropy into amorphous solids, since they do not reach their lowest energy state during crystallization.

Amorphous form of (S)-(+)-Clopidogrel bisulfate can be prepared by reacting (S)-(+) Clopidogrel free base in suitable solvents with concentrated sulfuric acid (80% to 98%) with molar ratio of 0.98 to 1.2 between −30° C. to 50° C. and applying vacuum for slow removal of solvents. The suitable solvents can be water, methanol, ethanol, propanol, n-butanol, dichloromethane, dimethyl formamide, dimethyl acetamide, 1,4-Dioxane, tetrahydrofuran and mixtures thereof. Removal of solvent(s) under vacuum leads to amorphous form of clopidogrel bisulfate as a powder or a brittle foam, which on mechanical agitation and subsequent drying gives processable dry amorphous solid.

Alternatively, amorphous form of (S)-(+)-Clopidogrel bisulfate can be prepared by reacting (S)-(+) Clopidogrel free base in suitable solvents with potassium hydrogen sulfate or sodium hydrogen sulfate with molar ratio of 1 to 4 between 20° C. to 35° C. and applying vacuum for slow removal of solvents. The suitable solvents can be water, methanol, ethanol, benzene, propanol, isopropanol, n-butanol, dichloromethane, dichloroethane, acetone, cyclohexane, dimethyl formamide, dimethyl acetamide, 1,4-Dioxane, tetrahydrofuran or a mixture thereof.

The process of manufacture of amorphous form of (S)-(+)-Clopidogrel bisulfate involves using a (S)-(+) Clopidogrel free base (% ee>99%), suitably employed solvent selected from ethanol, methanol, propanol, isopropanol, butanol, 1,4-dioxane, tetrahydrofuran, DMF, DMA, dichloromethane, acetone, cyclohexane, water and the like and conc. $H_2SO_4$ (80 to 98%) or potassium hydrogen sulfate (1-4 moles) in a suitable solvent, with or without inert atmosphere.

In a preferred embodiment of the present invention, the suitable solvents are ethanol, 1,4-dioxane, acetone, cyclohexane, THF, dichloromethane, water or a mixture thereof, which is removed under vacuum.

It is more preferred to use ethanol, acetone, dichloromethane, cyclohexane or water as a solvent, which is removed under reduced pressure.

Various processes employed to obtain the amorphous (S)-(+)-Clopidogrel bisulfate includes, solidification of the melt, spray drying, freeze drying, reduction of the particle size, lyophilization, removal of solvent from solvate or hydrates, rapid freezing, milling, grinding and cogrinding. Amorphous solid may also be prepared by the use of solvates and antisolvents. Some of the typical antisolvents can be pet-ether, ether, t-butyl methyl ether, diisopropyl ether, toluene, n-hexane, cyclohexane, n-heptane, hexane fraction, heptane fraction and such other non-polar solvents.

Amorphous (S)-(+)-Clopidogrel bisulfate can exist in anhydrous form as well as hydrated form or solvated form. In general, the hydrated forms are equivalent to anhydrous forms and intended to be encompassed within the scope of the present invention.

Seeding with Form I at a suitable stage of solvate formation, more particularly in a highly concentrated state, gives a material enriched with Form I with partial amorphous form. Use of 85% $H_2SO_4$, 90% $H_2SO_4$, 95% $H_2SO_4$ and 98% $H_2SO_4$, was found to be advantageous. Various polyethylene glycols (PEG) 200, 400, 800, 900, 1000, 1200, 2000 and 4000 were used as amorphous form stabilizer. The concentration of PEG's wt/wt. w.r.t. Clopidogrel free base was between 0.1 to 5%. Scratching of the supersaturated solution also results in the formation of Form I enriched amorphous (S)-(+)-Clopidogrel bisulfate. Seeding with Form II at a suitable stage of solvate formation, more particularly in a highly concentrated state, gives a material enriched with Form II with partial amorphous form. Scratching of the supersaturated solution also results in the formation of Form II enriched amorphous (S)-(+)-Clopidogrel bisulfate.

Alternatively, it has been found that the sequence of addition of the reagents and its various permutations and combinations in the reaction conditions can be altered by people skilled in the art to obtain the desired result. It has also been envisaged that the product can be achieved with/without an inert atmosphere of nitrogen, argon or helium. All the above processes are incorporated in the scope of the current invention for manufacturing of amorphous (S)-(+)-Clopidogrel bisulfate.

An alternate process to produce amorphous Clopidogrel bisulfate comprises: 1) melting of solid form of Clopidogrel bisulfate, 2) cooling the melt rapidly to get a solid, and if required, 3) grinding or milling of the solid drug substance produced in step (2) above to get a powder.

Another alternate process for the preparation of amorphous Clopidogrel bisulfate involves reacting (S)-(+) Clopidogrel free base in suitable solvents with aqueous dilute sulfuric acid (15% to 35%) between 20° C. to 40° C. and applying vacuum for slow removal of solvents. The suitable solvents can be water, methanol, ethanol, propanol, n-butanol, benzene, dichloromethane, dichloroethane, acetone, cyclohexane, dimethyl formamide, dimethyl acetamide, 1,4-Dioxane, tetrahydrofuran or mixtures thereof.

Melting of the solid form of the drug substance may be done by techniques known in the art such as heating in an oven or heating in a reactor with heated jacket and the like. Cooling can be achieved by cooling the reactor vessel jacket to required temperature or floating the melt containing container over a cold bath or liquid nitrogen and the like.

Grinding may be performed by any suitable method such as grinding in a pestle and mortar or in a suitable mill to get the powder of required consistency.

Characterization of Amorphous Form

The amorphous form of (S)-(+)-Clopidogrel bisulfate so obtained can be characterized by its melting point, physical characteristics, X-ray powder diffraction pattern, DSC, Thermogravimetric analysis, differential scanning calorimetry, diffused reflection IR absorption and/or by its solid state nuclear magnetic resonance spectrum. Some of the key representative data are attached herewith.

The following nonlimiting examples illustrate the inventor's preferred methods for preparing the amorphous S(+) clopidogrel bisulfate and related compounds discussed in the invention.

EXAMPLE 1

Crystalline S(+) Clopidogrel bisulfate 100 g was dissolved in 700 ml of ethanol with agitation at ambient temp. under nitrogen atmosphere and a clear solution was obtained. Subsequently solvent was removed slowly under vacuum with rotavapor at approx. 30 to 50° C. Foaming was observed during solvent removal. During the removal of last traces of solvent, a brittle glossy foam is obtained, which is broken mechanically into free flowing powder. The powder is further dried at 60-65° C. for 3 to 4 hours in the rotavapor and amorphous S(+) clopidogrel bisulfate (98 g, 98%) is obtained. The amorphous form was characterized by XRD, DSC, IR, SOR (1% MeOH)+54°, chemical purity (HPLC) 99.95% and chiral purity 99.7% (S-Isomer), m.p. 68 to 72%.

EXAMPLE 2

Above experiment was repeated in the same manner except the removal of solvent at rotavapor was replaced by concentrating ethanolic solution under vacuum and mechanical stirrer under above conditions. The product was found to be identical as in Ex. 1.

EXAMPLE 3

508 g of (+) clopidogrel (−) camphor sulfate (diastereoisomer salt) prepared as per WO 02/059128 Ex. 51/52/53, was dissolved into 200 ml of dichloromethane and the mixture is agitated for complete dissolution. Then a solution of 91 g of potassium carbonate in 700 ml of deionized water was introduced and vigorously agitated, so that pH of aqueous layer was ~8. The organic layer was separated and dried over anhydrous sodium sulfate, filtered and further concentrated to give 280 g of S(+) clopidogrel free base. Subsequently 1680 ml of ethanol was added and the mixture was stirred until a clear homogeneous solution was obtained. This solution was cooled externally 0 to 5° C. and 1 equivalent of 98% conc. $H_2SO_4$ was added slowly. Simultaneously vacuum was applied and the solution was concentrated initially at ~25° C. and subsequently at 40-50° C. under mild mechanical stirring. Once again, foam formation occurred, which was broken with mechanical agitation. Finally, the last traces of solvents were removed at 60-65° C. under high vacuum and 347 g (95%) amorphous S(+) clopidogrel bisulfate was obtained. The product was identical to the product obtained in Ex. 1.

EXAMPLE 4

S(+) Clopidogrel free base (2 g) was generated as per Ex. 3, and was dissolved in 20 ml of n-propanol at 80-85° C. and 1 eq. of 98% concen. $H_2SO_4$ was added. The solvent was distilled under vacuum and final traces of solvents were removed under 1-2 mm. vacuum at 60° C. (±5° C.) for 2 h, to give 2 g of amorphous S(+) clopidogrel bisulfate (77%). The product was identical to the product obtained in Ex. 1, except presence of residual OVI. (Organic Volatile Impurities)

Similar experiments were repeated with tert-butanol, n-butanol, 1,4-Dioxane, tetrahydrofuran, isopropyl alcohol, dichloromethane and mixtures thereof.

EXAMPLE 5

114 g of (+) clopidogrel (−) camphor sulfate (diastereoisomeric salt prepared as per WO 02/059128 Ex. 51/52/53) was dissolved into 450 ml of dichloromethane and aqueous layer was basified with sodium bicarbonate until basic pH ~8. Organic layer was extracted and washed twice with 2×100 ml deionized water. Subsequently organic layer was collected and dried over anhydrous sodium sulfate, filtered and the filtrate was concentrated to give 63 g (95%) of S(+) Clopidogrel free base. Acetone 380 ml was added to it at ambient temp. and stirred until a clear solution was obtained. 1.26 g of polyethylene glycol-200 (PEG-200), as amorphous form stabilizer or as crystallization inhibitor, was added to the reaction mixture and the whole solution was cooled externally to −5 to 0° C., to which 1 eq. of 98% of concentration $H_2SO_4$ was added in 5 to 7 min. This solution was immediately rotavapored under mild vacuum and the solution was concentrated. Once again, glossy brittle foams were observed during the final stages of drying. The final traces of solvent was removed by drying the powder at 55-60° C. under vacuum 1 mm for 3 h, to give 79.5 g (96%) of amorphous (+) clopidogrel bisulfate. The drug substance was identical to the product obtained in Ex. 1, except residual OVI (Organic volatile impurities).

EXAMPLE 6

(Includes Variations of Several Examples)

The experiment was repeated in a similar manner as described in Ex. 5, except the fact that PEG 200 was changed to PEG-400 (2% w/w w.r.t. S(+) clopidogrel free base) and Similarly, several experiments were conducted with PEG-600, PEG-800, PEG-900, PEG-1000, PEG-1200, PEG-2000, PEG-4000 and PEG-6000. The concentration of PEG's wt/wt-w.r.t. free base was varied between 0.1% to 5%.

Similarly, another variations to above experiments was used of 90% $H_2SO_4$, 95% $H_2SO_4$ and 85% $H_2SO_4$, instead of 98% $H_2SO_4$, to make amorphous S(+) clopidogrel bisulfate with various other PEG's already mentioned above, gave invariably pharmaceutically processable amorphous material. However, the mol. ratio of above $H_2SO_4$ w.r.t. free base was always between 0.95 to 1.2.

In quality terms i.e., XRD, DSC, chiral purity, chemical purity, IR, the product obtained via above methods was always amorphous free flowing processable solid.

EXAMPLE 7

Polymorph I of (+)-Methyl(2-chlorophenyl)-(6,7-dihydro-4H-thieno[3,2-c]pyrid-5-yl)acetate bisulfate salt (I)

2.1 g (+)-Methyl(2-chlorophenyl)-(6,7-dihydro-4H-thieno[3,2-c]pyrid-5-yl)acetate was added 7.6 mL of acetone to obtain a clear solution. To this solution, 0.887 g of $H_2SO_4$ (80%) was added slowly and temperature was maintained around 20° C. under nitrogen atmosphere. Later the reaction mixture was cooled up to −20° C. for 2 hrs and then the temperature was brought to room temperature (20° C.). The reaction mixture was stirred at 20-25° C. Precipitate was isolated (600 mg), dried under vacuum at temperature not exceeding 50° C.

The product obtained was characterized by different physico-chemical characteristics and was found identical to Form I as described in the literature, having characteristics as given below;
SOR ($\alpha^D$): +54.03° (C=1.89, MeOH)
Melting point: 185° C.±1° C.
Chiral Purity: 99.63% (ee)
IR and XRD were found matching to that reported in the literature.

EXAMPLE 8

Polymorph I of (+)-Methyl(2-chlorophenyl)-(6,7-dihydro-4H-thieno[3,2-c]pyrid-5-yl)acetate bisulfate salt (I)

To 2 g (+)-Methyl(2-chlorophenyl)-(6,7-dihydro-4H-thieno[3,2-c]pyrid-5-yl)acetate was added 5 mL of acetone and stirred at 25-30° C. The temperature of the reaction mixture was raised from 25 to 65° C. and then kept at 65° C. for 5 min. At temperature 50-52° C. 0.676 g of concentrated $H_2SO_4$ was added. The reaction mixture was cooled from 52° C. to 5° C., and additional acetone was added and stirred for 5 min. Later the reaction mixture was stirred at 25-30° C. for 12 hrs, the thick precipitate obtained was filtered, washed with 5 mL of acetone and the residue was dried in a vacuum oven. The yield of titled product obtained was 1.27 g (47%).

The product obtained was characterized by different physico-chemical characteristics and was found identical to Form I as described in the literature, having characteristics, as given below;
SOR ($\alpha^D$): +54.03° (C=1.89, MeOH)
Melting point: 185° C.±1° C.
Chiral Purity: 99.80% (ee)
IR and XRD were found matching to that reported in the literature.

EXAMPLE 9

Polymorph I of (+)-Methyl(2-chlorophenyl)-(6,7-dihydro-4H-thieno[3,2-c]pyrid-5-yl)acetate bisulfate salt (I)

To 1.98 g (+)-Methyl(2-chlorophenyl)-(6,7-dihydro-4H-thieno[3,2-c]pyrid-5-yl)acetate was added 5 mL of acetone and stirred at 25-30° C. The temperature of the reaction mixture was raised from 25 to 50-52° C. and within one lot 0.7 g of concentrated $H_2SO_4$ (95%) was added with constant stirring and the reaction mixture was suddenly cooled to 0° C. to −5° C. for 10 min. Later the reaction mixture was stirred at 25-30° C. for 12 hrs, the thick precipitate obtained was filtered, washed with 5 mL of acetone and the residue (1.6 g, 62%) was dried in a vacuum oven.

The product obtained was characterized by different physico-chemical characteristics and was found identical to Form I as described in the literature, having characteristics as given below;
SOR ($\alpha^D$): +55.96° (C=1.89, MeOH)
Melting point: 185° C.±1+ C.
Chiral Purity: 99.85% (ee)
IR and XRD were found matching to that reported in the literature.

EXAMPLE 10

Crystalline S(+) clopidogrel bisulfate 10 g was dissolved into 100 ml of ethanol at ambient temp. until a clear solution was obtained. Vacuum was applied and the solution was concentrated at 50-55° C., until a dense thick liquid is obtained. In the presence of ethanol, the brittle foam collapses into dense thick liquid. To this, 5% by wt. i.e. 500 mg of S(+) clopidogrel bisulfate Form I (see Ex. 7/8/9) was added as a seed and subsequently the concentrated heterogenous thick liquid is concentrated at 55° C. under high vacuum. Once again glossy brittle foam is observed during the drying of final traces of solvents and after breaking the foam mechanically, the solid was further dried for 3 h at 60-65° C. to give amorphous S(+)clopidogrel with impurities of Form I (9.5 gm 95%), m.p. 160-168° C.

EXAMPLE 11

Crystalline S(+) Clopidogrel bisulfate 10 g was dissolved into 100 ml of ethanol at ambient temp. until a clear solution was obtained. Vacuum was applied and the solution was concentrated at 50-55° C., until a dense thick liquid is obtained. In the presence of ethanol, the brittle foam collapses into dense thick liquid. To this, 10% by wt. i.e. 1000 mg of S(+)

clopidogrel bisulfate Form I (see Ex. 7/8/9) was added as a seed and subsequently the concentrated heterogenous thick liquid is concentrated at 55° C. under high vacuum. Once again glossy brittle foam is observed during the drying of final traces of solvents and after breaking the foam mechanically, the solid was further dried for 3 h at 60-65° C. to give amorphous S(+)clopidogrel with impurities of Form I (9.5 gm 95%), m.p. 160-168° C.

EXAMPLE 12

A solution of 10 g of S(+) Clopidogrel free base in 50 ml of ethanol was cooled to –5 to 0° C. and conc. $H_2SO_4$ 1 eq. was added to it which was spray dried in a 'spray Dryer (Jay Instruments & Systems, LSD-48) with 45-50 mm of water aspirator with a flow rate of 10-10.5 ml/min. with inlet temp. 60° C. and outlet temp. 35-40° C. and 5 g of amorphous Clopidogrel bisulphate was obtained. This substance was identical in every respect.

EXAMPLE 13

(Molt+Form I)

To a molt of 10 g of amorphous S(+) Clopidogrel bisulfate as prepared in previous examples at 100° C. (±10° C.), seed of 1 g of Form I of Clopidogrel bisulfate is added and the seeded molt is cooled slowly to room temperature with vigorous stirring. 10.5 g of amorphous Clopidogrel with impurities of Form I is obtained.

EXAMPLE 14

(Includes Variations of Several Examples)

To 10 g of S(+) Clopidogrel free base, 5-6 volume of acetone is added. The mixture is cooled to 0 to 5° C. and 1 eq. of 98% conc. $H_2SO_4$ and then PEG-200 (Form stabilizer) was added. The solution was concentrated to approximately 15 g. and 5% wt/wt of Form I (Ex. 7/8/9) was added as seed.

Similarly, several experiments were conducted with PEG-400, PEG-1000, PEG-2000 and PEG-4000. The concentration of PEG wt/wt. w.r.t. free base was varied between 0.2% to 5%. Similarly, another variation to above experiments was the use of 10% and 20% of Form I as seed along with various other PEG's mentioned above. This gave amorphous and Form I in 10 g to 12 g yield depending on amount of Form I used. Mixture of amorphous and Form I is prepared in varied proportions.

EXAMPLE 15

Crystalline Form II of S(+) Clopidogrel hydrogen sulfate (110 g, 0.262 mole) was dissolved in a mixture of dichloromethane (1.1 L) and water (132 mL) under stirring at 25-30° C., and then evaporated to dryness. The operation of addition of dichloromethane to the reaction mixture and evaporation was repeated to remove most of the water and then traces of water was removed under reduced pressure (10-15 mm) at 50-55° C. The solid obtained was dried at 50-55° C. for 8 hours to get amorphous Clopidogrel bisulfate (111.6 g). The amorphous form was characterized by XRD, DSC, IR, chemical purity (HPLC)>99% and chiral purity 99.38% (S-Isomer), % water 1.47, m.p. 122-126° C. (softens).

EXAMPLE 16

S(+) Clopidogrel hydrogen sulfate (Form I) (25 g, 0.059 mole) was similarly treated as described in Experiment 15 above to give 26 g amorphous clopidogrel hydrogen sulfate. The amorphous form was similarly characterized by XRD, DSC, IR, chemical purity (HPLC)>99% and chiral purity (chiral HPLC) 99.84% (e.e.), % water 1.5, m.p. 124-126° C. (softens).

EXAMPLE 17

To a stirred suspension of clopidogrel base (38.31 g, 0.119 mole) in water (30 mL), was added potassium hydrogen sulfate (32.3 g, 0.237 mole) at 25-30° C. The reaction mixture was stirred for 15 minutes and acetone (250 mL) was added, stirred further for 30 minutes and filtered. Insoluble solid was filtered. The filtrate was distilled at 50-55° C. under reduced pressure (5-10 mm). Dichloromethane (380 mL) was added and distilled at 50-55° C. This operation was repeated twice by adding dichloromethane (350 mL), and finally traces of water was removed under reduce pressure (5-10 mm) to give amorphous clopidogrel hydrogen sulfate (46 g). The amorphous form was similarly characterized by XRD, DSC, IR, chemical purity (HPLC)>99% and chiral purity (chiral HPLC) 99.8% (e.e.), % water 1.91, m.p. 132-135° C. (softens).

EXAMPLE 18

To a stirred suspension of clopidogrel base (3.83 g, 0.0119 mole) in water (3 mL) was added potassium hydrogen sulfate (1.62 g, 0.0119 mole) at 25-30° C. The reaction mixture was stirred for 15 minutes and acetone (25 mL) was added, further stirred for 30 minutes and filtered. The filtrate was distilled at 50-55° C. under reduce pressure (5-10 mm). Benzene (10 mL) was added to the reaction mixture and distilled at 90-95° C., di-isopropyl ether (20 mL) was added and stirred at 25-30° C. for 1 hour and filtered. The semi sold material was dissolved in dichloromethane (25 mL) and distilled under reduced pressure (5-10 mm) to give clopidogrel hydrogen sulfate (2.1 g). The amorphous form was similarly characterized by XRD, DSC, IR, chemical purity (HPLC)>99% and chiral purity (chiral HPLC) 99.5% (e.e.), % water 3.0, m.p. 94-98° C. (softens).

EXAMPLE 19

Amorphous Clopidogrel hydrogen sulfate (23 g, m.p. 132-35° C.) was melted under reduced pressure (2-5 mm). The molten mass was cooled to 25-30° C. at reduced pressure. Subsequently, the vacuum was released under nitrogen atmosphere and the amorphous Clopidogrel bisulfate was isolated (21 g). The amorphous form was similarly characterized by XRD, DSC, IR, chemical purity (HPLC)>99% and chiral purity (chiral HPLC) 99% (e.e.), % water 0.34, m.p. 88-90° C. (softens).

EXAMPLE 20

To a solution of Clopidogrel free base (13 g, 0.04 moles) in acetone (85 ml) at 25-30° C. was added dropwise dilute aqueous sulfuric acid (3.56 g, 0.036 mole). The solution was stirred for 15 minutes, distilled at 50-55° C. under reduced pressure (5-10 mm). Dichloromethane (130 ml) was added and distilled, the operation was repeated using dichloromethane (130 ml). Finally traces of water was removed under reduced pressure (5-10 mm) to give amorphous clopidogrel hydrogen sulfate (16.4 g). The amorphous form was similarly characterized by XRD, DSC, IR, chemical purity (HPLC)>99% and chiral purity (chiral HPLC) 99.4% (e.e.), % water 3.37, m.p. 128-130° C. (softens).

EXAMPLE 21

To a solution of Clopidogrel free base (10 g, 0.031 moles) in acetone (65 ml) and water (13 ml), was added dropwise sulfuric acid (3.0 g, 0.33 mole) at 25-30° C. The solution was stirred for 15 minutes, distilled at 50-55° C. under reduced pressure (5-10 mm). Dichloromethane (100 ml) was added and distilled, the operation was repeated twice using dichloromethane (100 ml). Finally traces of water was removed under reduced pressure (5-10 mm) to give amorphous clopidogrel hydrogen sulfate (13.7 g). The amorphous form was similarly characterized by XRD, DSC, IR, chemical purity (HPLC)>99% and chiral purity (chiral HPLC) 99.8% (e.e.), % water 1.95, m.p. 110-120° C. (softens).

EXAMPLE 22

Amorphous Clopidogrel hydrogen sulfate prepared above (1.2 g) was stirred in ethyl acetate (36 ml) for 30-45 minutes and distilled to dryness (oily residue). The oily residue was stirred in ethyl acetate (36 ml) at 20-25° C. and filtered to give Form II of S-(+) Clopidogrel hydrogen sulfate (0.5 g, m.p. 169-175° C., chemical purity (HPLC) 98% and chiral purity (chiral HPLC) 99.8% (e.e.))

EXAMPLE 23

Amorphous Clopidogrel hydrogen sulfate prepared above (0.2 g) was stirred in acetone (3 ml) for 16 hours and filtered, washed with acetone and dried to give Form II of S-(+) Clopidogrel hydrogen sulfate (0.12 g, m.p. 174-177° C.).

DESCRIPTION OF ATTACHMENTS

XRD represents X-ray diffractogram. The horizontal axis represents 2θ and the vertical axis represents the peak intensity.

Figure 3:
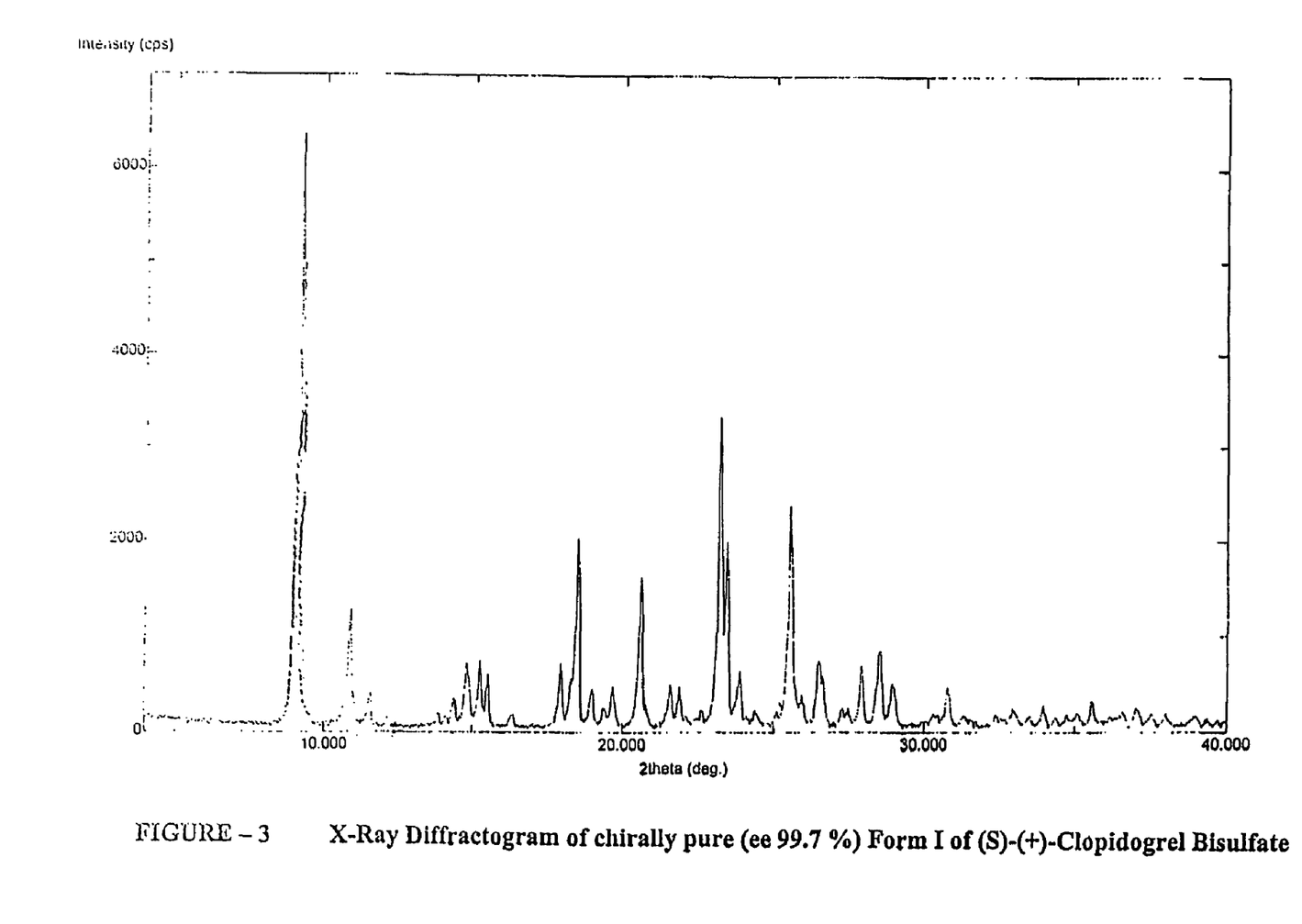
FIG. 3 XRD of Form I (chirally pure ee 99.7%).
4.
Figure 4:
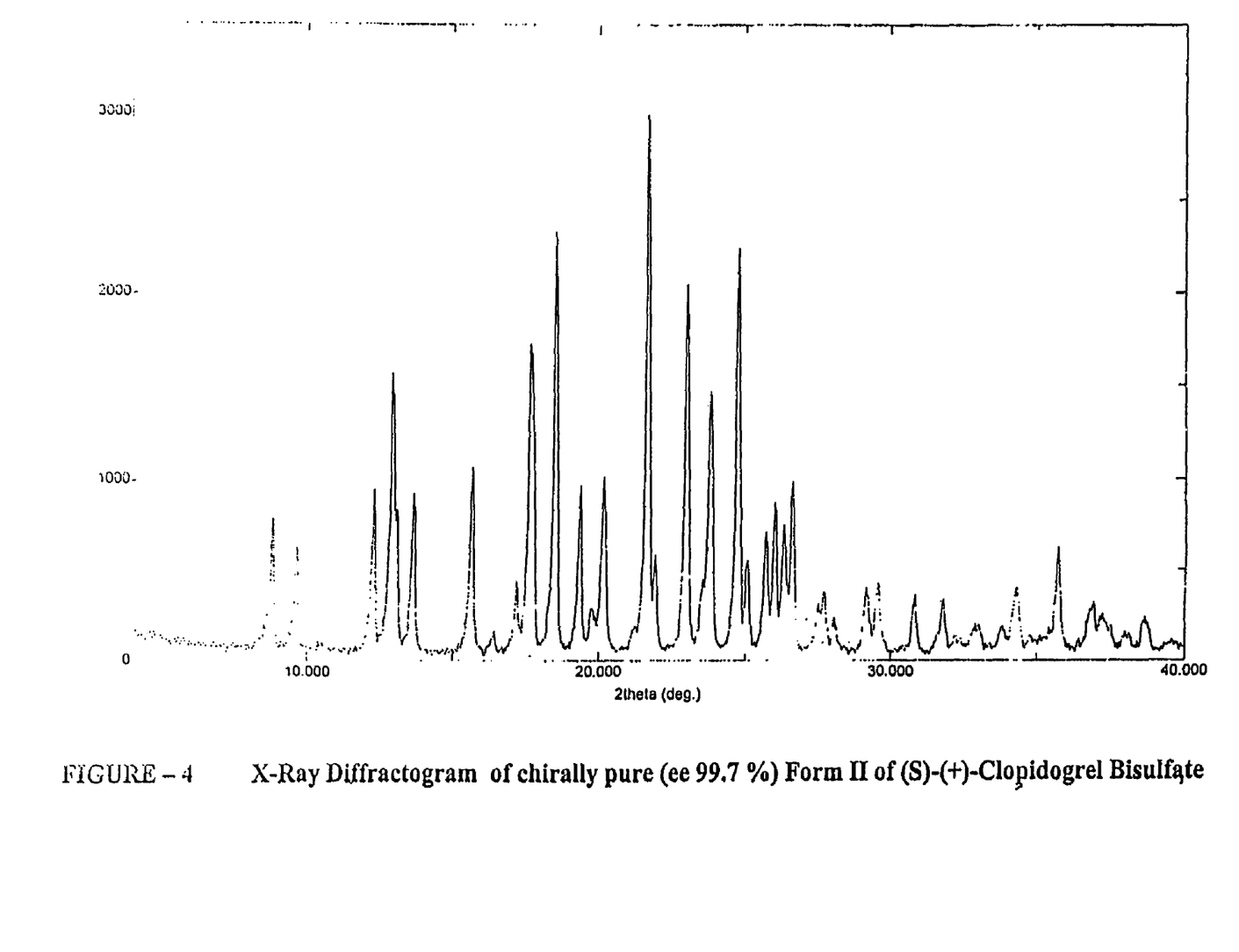
FIG. 4 XRD of Form II (chirally pure ee 99.5%).
5.
Figure 5:
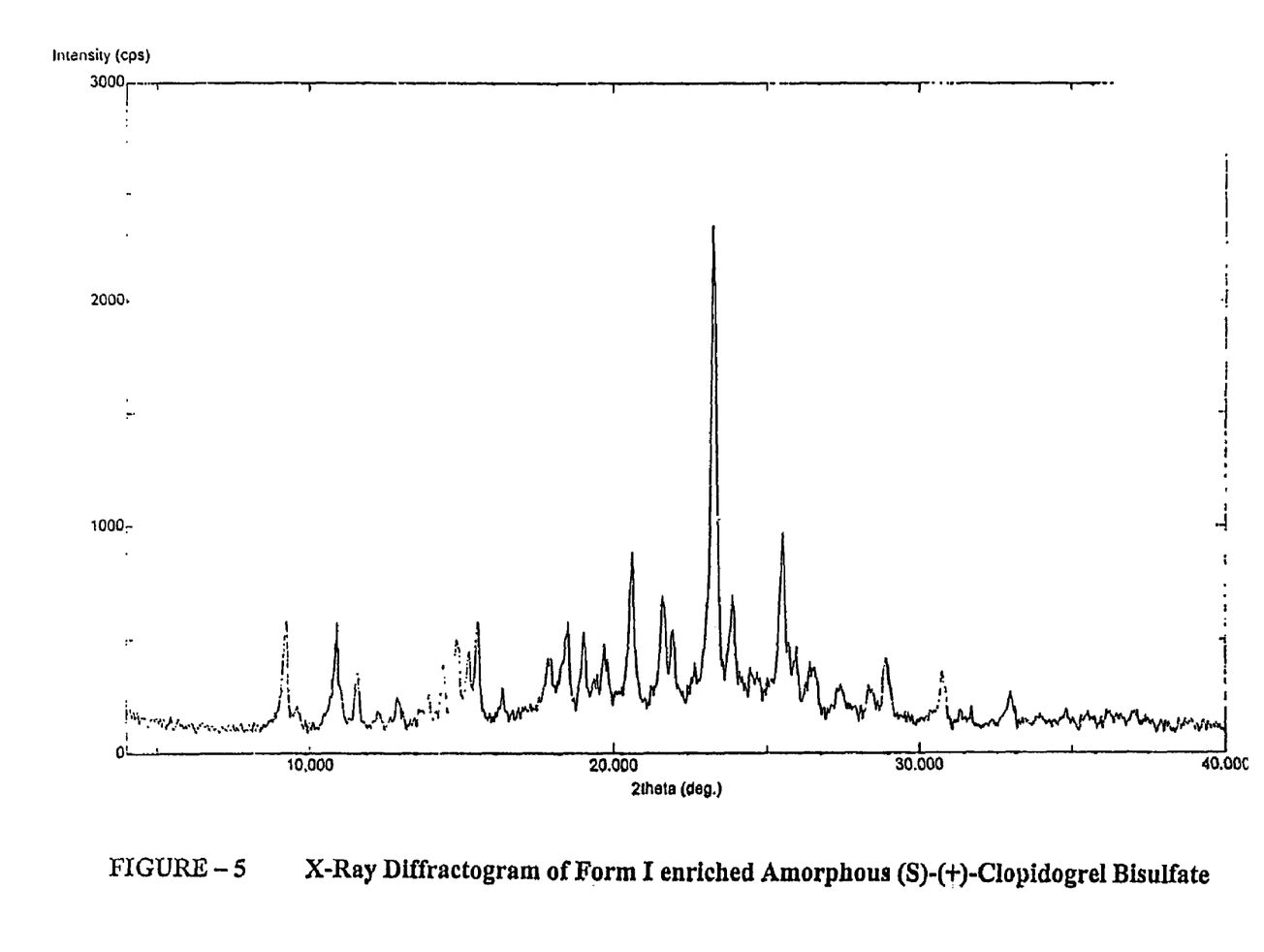
FIG. 5 XRD of Form I enriched amorphous solid
6.
Figure 6:
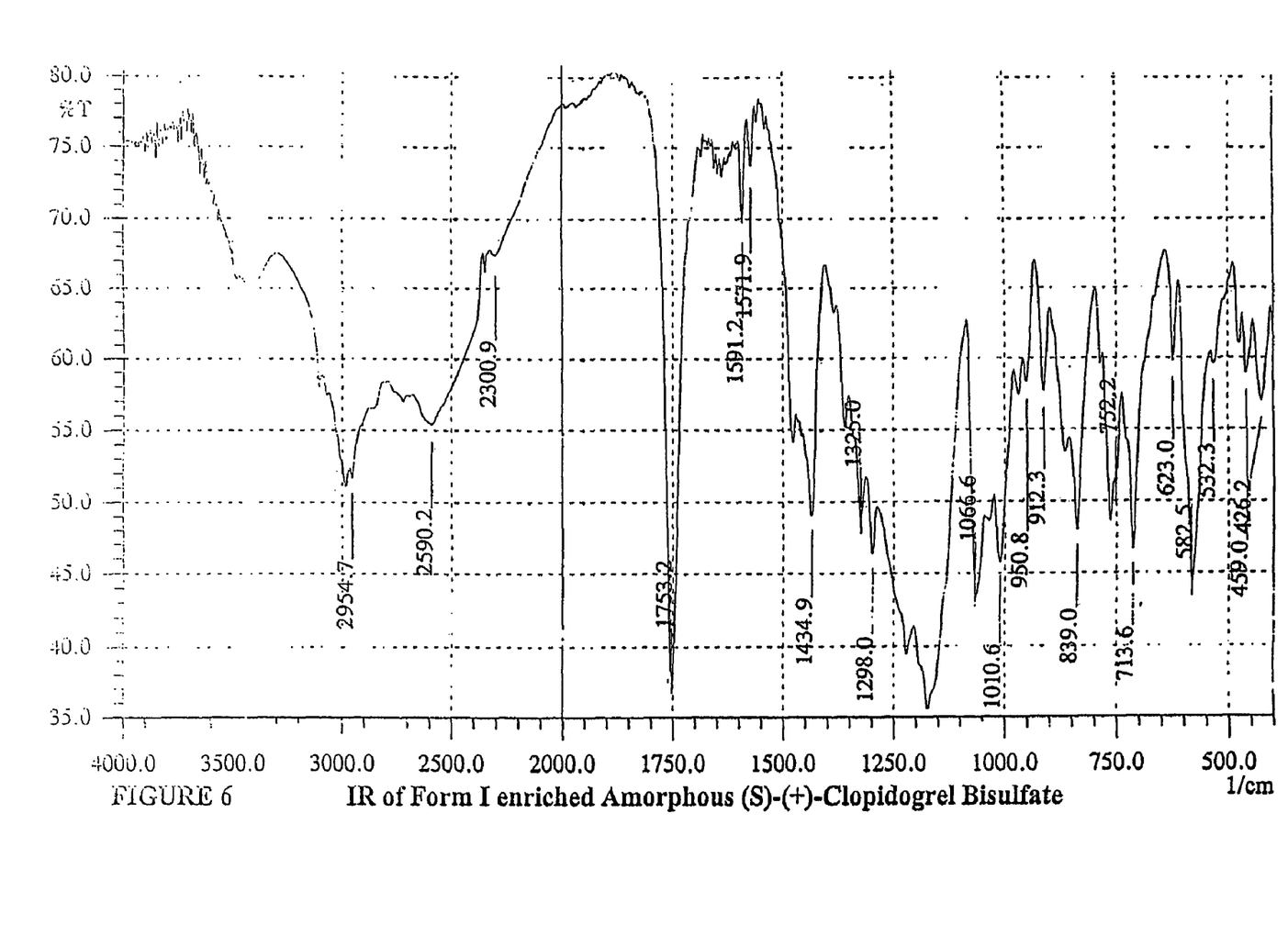
FIG. 6 IR of Form I enriched amorphous Solid.

The powder X-ray diffraction pattern of the amorphous form of the present invention shows no peaks (FIG. 1) which are characteristic of the crystalline forms of the Clopidogrel bisulfate (FIG. 3 and FIG. 4), thus demonstrating the amorphous nature of the drug substance.

The amorphous S-(+) Clopidogrel bisulfate of the present invention is water soluble. The amorphous S-(+) Clopidogrel bisulfate of the present invention is also easy to handle and formulate into various pharmaceutical compositions.

Formulation

The amorphous Clopidogrel drug substance of the present invention prepared according any process described above or any other process can be administered orally, parenterally or rectally without further formulation, or as a simple solution in water or any pharmaceutically acceptable liquid carrier. The drug substance of the present invention may also be filled in a capsule directly for oral administration. However, it is preferred that the drug substance is formulated with one or more excipients to prepare a pharmaceutical composition, for example, an oral dosage form.

Another aspect of the present invention aims at providing the various pharmaceutical compositions of amorphous (S)-(+)-Clopidogrel bisulfate containing active ingredients.

According to the present invention, amorphous (S)-(+)-Clopidogrel bisulfate is formulated in pharmaceutical compositions for oral use containing required amount of the active ingredient per unit of dosage, in combination with at least one pharmaceutical excipient in the form of tablets, sugar coated tablets, capsules, injectable solutions, granules or a syrup. It can also be administered rectally in the form of suppositories or can be parentally administered in the form of an injectable solution.

In the form of tablets, it can be administered in a solid composition by mixing the principal active ingredient with a pharmaceutical vehicle, such as gelatin, lactose magnesium stearate, talc, Arabic gum or amidon, and can be coated with saccharose or other appropriate materials or can be treated so as to ensure prolonged activity and controlled or sustained release in a continuous manner by predetermining the quantity of the principal active ingredient.

In the case of powders or granules, an active ingredient mixed with some dispersion agents or dampening agents, or suspending agents like polyvinylpyrrolidone, along with some sweetening substances or taste correctors are employed.

The capsule form can be easily attained by mixing the active ingredient with a dilutant and by pouring the mixture obtained in soft or hard capsules. The active ingredient can be formulated in the form of microcapsules, possibly with one or more supports or additives.

In an embodiment of the present invention, there is provided a Clopidogrel bisulfate-crystallization inhibitor composite which comprises of the amorphous drug substance along with at least one crystallization inhibitor in an intimate association. Crystallization inhibitors include any material which reduces the conversion of the amorphous Clopidogrel bisulfate to crystalline form, such as, polymers, carbohydrates, lipids and the like. Some examples are polyvinylpyrrolidone, hydroxypropylmethylcellulose (HPMC), ethyl cellulose, sodium or calcium carboxymethylcellulose, hydroxyethylcellulose, HPMC phthalate, dextran, β-cyclodextrin, polyvinyl alcohol, polyethylene glycol, block copolymers of ethylene oxide or propylene oxide, acacia, starch and the like. It is understood that the stability of the amorphous composite is influenced by the crystallization inhibitor(s) as well as the quantity used. The drug-crystallization inhibitor composite of the present invention can be prepared by any suitable process but not limited to the ones known in the art. Aqueous suspensions, saline solutions or sterile and injectable solutions can be employed for parental administration.

For rectal administration the formulation would constitute the use of suppositors as the principal active ingredient, which can be prepared with binders melting at the rectal temperature, for example cocoa butter or polyethylene glycols.

In another embodiment of the present invention a method of treatment and use of the new polymorphs of Clopidogrel for the treatment of cardiovascular disorders is provided, comprising administering, for example, orally or in any other

We claim

Figure 1:
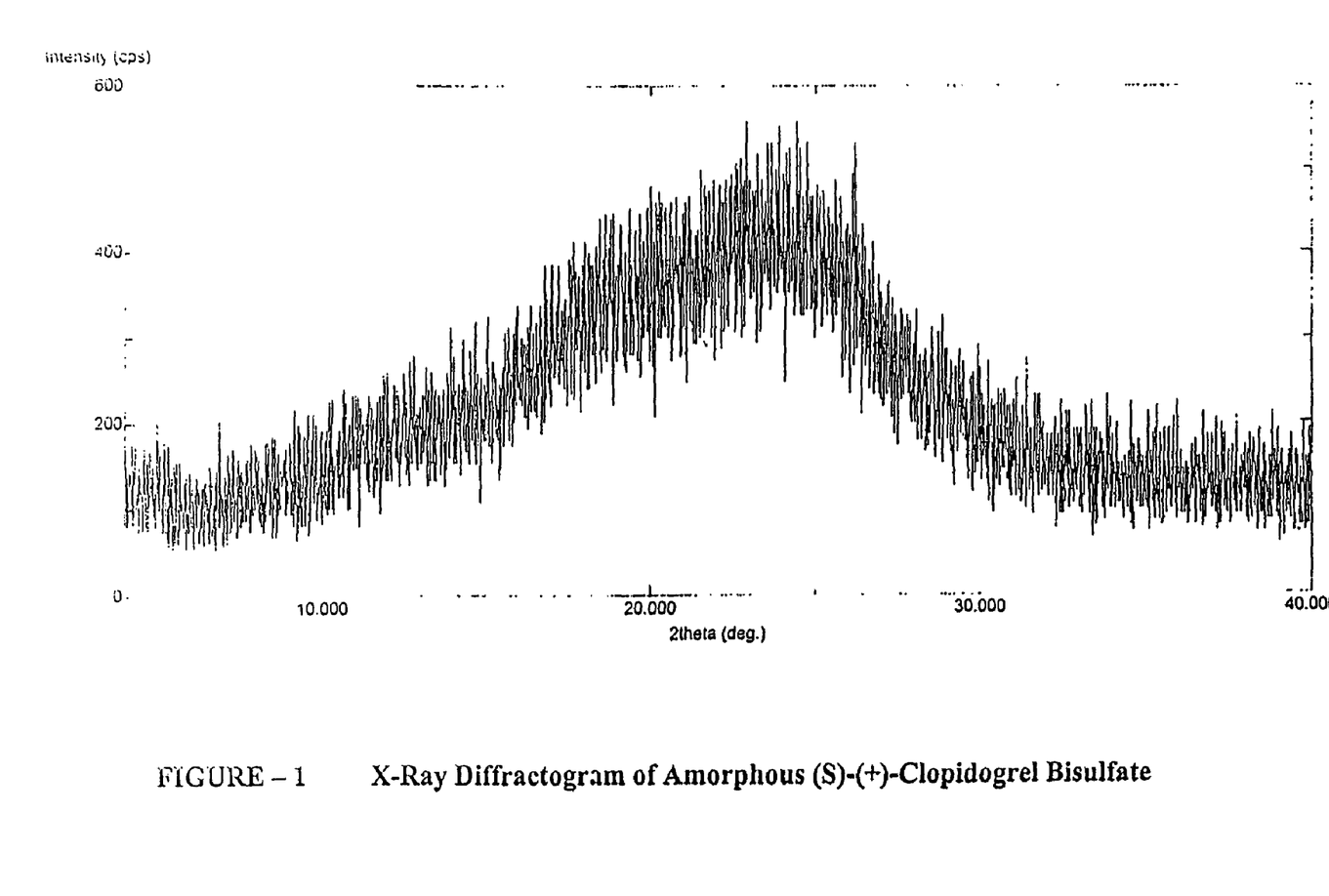
FIG. 1 XRD of amorphous (S)-(+)-Clopidogrel bisulfate.
2.
Figure 2:
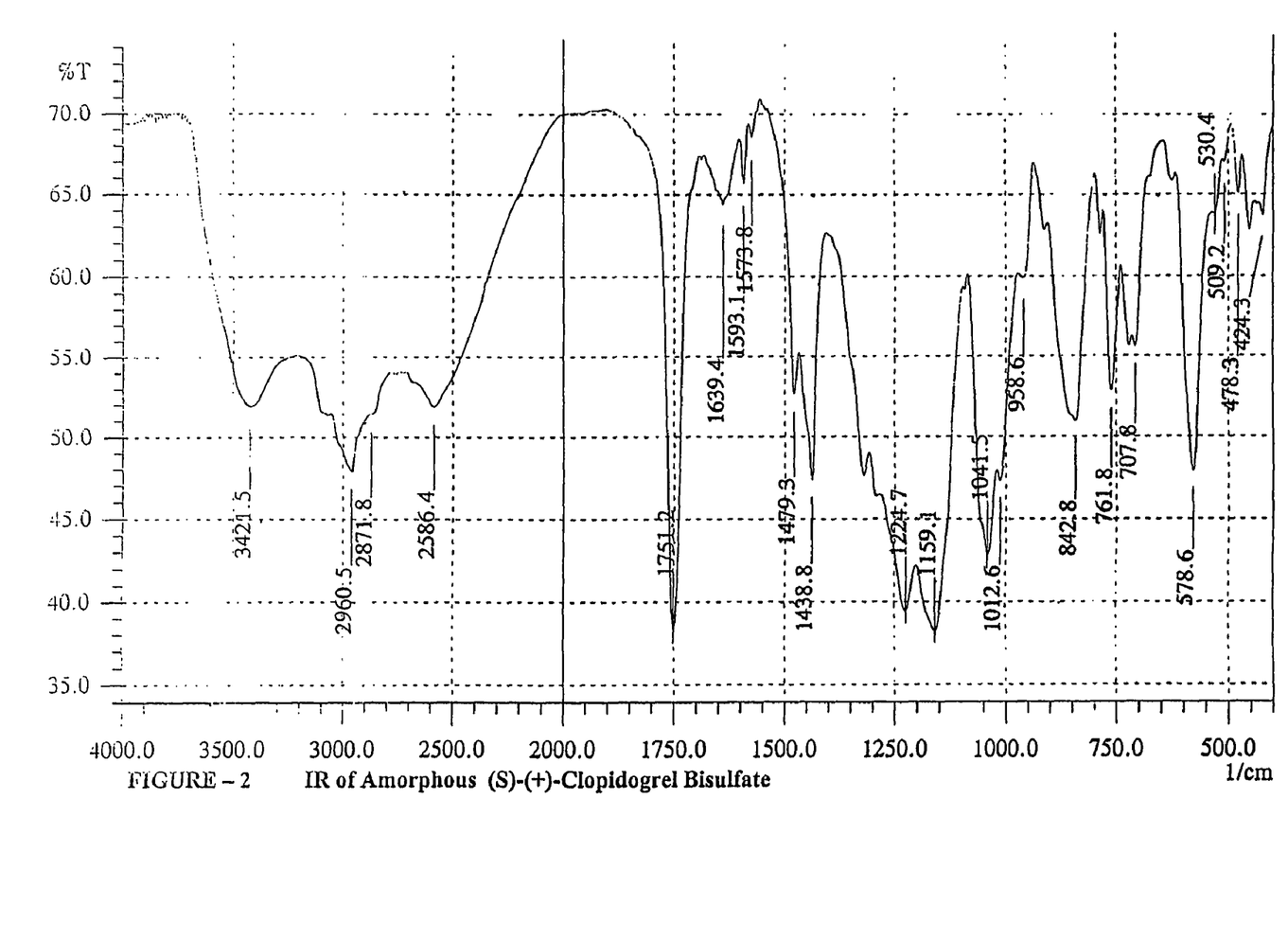
FIG. 2 IR of amorphous (S)-(+)-Clopidogrel bisulfate.
3.

1. Amorphous S-(+) Clopidogrel bisulfate in hydrated form containing about 1-4% water and having a powder X-ray diffraction pattern substantially as depicted in FIG. 1.

2. A composition of Form I of S-(+) Clopidogrel bisulfate enriched with amorphous S-(+) Clopidogrel bisulfate.

3. A composition of Form II of S-(+) Clopidogrel bisulfate enriched with amorphous S-(+) Clopidogrel bisulfate.

4. A process for preparation of amorphous S-(+) Clopidogrel bisulfate which comprises reacting S-(+) Clopidogrel base in suitable solvents with concentrated sulfuric acid and subsequently slowly removing the solvents.

5. A process as claimed in claim 4, wherein the molar ratio between S-(+) Clopidogrel base and sulfuric acid is between 0.98 and 1.2.

6. The process as claimed in claim 4 wherein the reaction between the S-(+) Clopidogrel base and concentrated acid is carried out at a temperature between 0° C. and 5° C.

7. The process as claimed in claim 4 wherein suitable solvents are selected from the group consisting of methanol, ethanol, propanol, isopropanol, n-butanol, dichloromethane, dichloroethane, dimethyl formamide, dimethyl acetamide, 1,4-Dioxane, tetrahydrofuran, and mixtures thereof.

8. A process as claimed in claim 5 wherein the solvent used is ethanol.

9. A process for preparation of amorphous S-(+) Clopidogrel bisulfate which comprises reacting S-(+) Clopidogrel free base in suitable solvents and water with concentrated sulfuric acid and subsequently slowly removing the solvents.

10. The process as claimed in claim 9 wherein the solvents used is acetone and dichloromethane or cyclohexane.

11. A process for preparation of amorphous S-(+) Clopidogrel bisulfate which comprises reacting S-(+) Clopidogrel base in suitable solvents with aqueous dilute sulfuric acid and subsequently slowly removing the solvents.

12. A process as claimed in claim 10, wherein the molar ratio between S-(+) Clopidogrel base and sulfuric acid is between 1 to 0.9.

13. The process as claimed in claim 11 wherein the reaction between the S-(+) Clopidogrel base and dilute sulfuric acid is carried out at a temperature between 20° C. and 35° C.

14. The process as claimed in claim 11 wherein suitable solvents are selected from the group consisting of water, methanol, ethanol, propanol, isopropanol, n-butanol, acetone, dichloromethane, dichloroethane, cyclohexane, dimethyl formamide, dimethyl acetamide, 1,4-Dioxane, tetrahydrofuran, and mixtures thereof.

15. A process as claimed in claim 14 wherein the solvent used is acetone and dichloromethane.

16. A process for preparation of amorphous S-(+) Clopidogrel bisulfate which comprises reacting S-(+) Clopidogrel base in suitable solvents with sodium hydrogen sulfate or potassium hydrogen sulfate and subsequently slowly removing the solvents.

17. A process as claimed in claim 16, wherein the molar ratio between S-(+) Clopidogrel base and sodium hydrogen sulfate or potassium hydrogen sulfate is between 1 to 2.

18. The process as claimed in claim 16 wherein the reaction between the free base and salt is carried out at a temperature between 20° C. and 35° C.

19. The process as claimed in claim 16 wherein suitable solvents are selected from the group consisting of water, methanol, ethanol, propanol, isopropanol, n-butanol, acetone, dichloromethane, dichloroethane, cyclohexane, dimethyl formamide, dimethyl acetamide, 1,4-Dioxane, tetrahydrofuran, and mixtures thereof.

20. A process as claimed in claim 17 wherein the solvent used is acetone, water and dichloromethane.

21. A process of preparing amorphous S-(+) Clopidogrel busulfate which comprises melting the amorphous S-(+) Clopidogrel bisulfate obtained from the process of claim 4 at elevated temperatures and subsequently cooling the molten form.

22. A process of preparing Form I of S-(+) Clopidogrel bisulfate enriched with amorphous form comprising seeding with Form I at a suitable stage of solvate formation, preferably in a highly concentrated state.

23. A process of preparing Form II of S-(+) Clopidogrel busilfate enriched with amorphous form comprising seeding with Form II at a suitable stage of solvate formation, preferably in a highly concentrated state.

24. The process as claimed in claim 22 wherein suitable solvates are selected from the group consisting of hydrates, ethanolates, and methanolates.

25. A process for the preparation of amorphous S-(+) Clopidogrel bisulfate wherein a Clopidogrel bisulfate-crystallization inhibitor composite, which comprises the amorphous drug substance along with at least one crystallization inhibitor which includes any material which reduces the conversion of the amorphous Clopidogrel bisulfate to crystalline form, such as polymers, carbohydrates, lipids and the like, in an intimate association is used.

26. A process as claimed in claim 25 wherein the crystallization inhibitor is selected from the group consisting of PEG 200, PEG 400, PEG 1000, and PEG 2000.

27. A process as claimed in claim 25 wherein concentration of the crystallization inhibitor vary from 0.1 to 5% wt/wt.

28. A process as claimed in claim 22 wherein the Form I and amorphous form are present in a ratio ranging from 0:100 to 99:1.

29. A process as claimed in claim 23 wherein the Form II and amorphous form are present in a ratio ranging from 0:100 to 99:1.

30. A process of converting amorphous S-(+) Clopidogrel bisulfate as claimed in claim 1 to Form II of S-(+) Clopidogrel bisulfate by stirring in a suitable solvent selected from the group consisting of acetone, benzene, and ethyl acetate.

31. A pharmaceutical composition comprising amorphous S-(+) Clopidogrel bisulfate as claimed in claim 1.

32. A pharmaceutical dosage form comprising a pharmaceutical composition of amorphous S-(+) Clopidogrel bisulfate.

33. A method of treatment comprising administering a composition of amorphous S-(+) Clopidogrel bisulfate in a therapeutically effective amount for the treatment of a cardiovascular disorder.

* * * * *